(12) United States Patent
Ariga

(10) Patent No.: US 9,032,784 B2
(45) Date of Patent: May 19, 2015

(54) HARDNESS TESTER FOR MAINTAINING IMAGE RESOLUTION BY USING IMAGE CLIPPING

(75) Inventor: Kozo Ariga, Tokyo (JP)

(73) Assignee: Mitutoyo Corporation, Kanagawa (JP)

( * ) Notice: Subject to any disclaimer, the term of this patent is extended or adjusted under 35 U.S.C. 154(b) by 303 days.

(21) Appl. No.: 13/570,392

(22) Filed: Aug. 9, 2012

(65) Prior Publication Data

US 2013/0047713 A1 Feb. 28, 2013

(30) Foreign Application Priority Data

Aug. 30, 2011 (JP) .................. 2011-188460

(51) Int. Cl.
*G01N 3/48* (2006.01)
*G01N 3/06* (2006.01)
*G01N 3/40* (2006.01)
*G06T 7/00* (2006.01)

(52) U.S. Cl.
CPC .................. *G01N 3/068* (2013.01); *G01N 3/40* (2013.01); *G06T 7/0002* (2013.01); *G01N 2203/0647* (2013.01)

(58) Field of Classification Search
CPC ... G01N 3/00; G01N 2203/0078; G01N 3/40; G06T 2210/22; G06T 2207/20132; G06T 7/0002
USPC ............................. 73/81; 382/298, 141, 152
See application file for complete search history.

(56) References Cited

U.S. PATENT DOCUMENTS

| | | | | |
|---|---|---|---|---|
| 5,146,779 A | * | 9/1992 | Sugimoto et al. ................. | 73/81 |
| 8,238,633 B2 | * | 8/2012 | Ida et al. ....................... | 382/128 |
| 8,401,339 B1 | * | 3/2013 | Anderson ...................... | 382/298 |
| 8,508,550 B1 | * | 8/2013 | Jenny ............................ | 345/620 |
| 2005/0265593 A1 | * | 12/2005 | Hauck et al. .................. | 382/141 |
| 2012/0085154 A1 | | 4/2012 | Takemura et al. | |
| 2012/0087567 A1 | | 4/2012 | Takemura et al. | |

FOREIGN PATENT DOCUMENTS

JP 2003-166923 6/2003

* cited by examiner

*Primary Examiner* — Hezron E Williams
*Assistant Examiner* — Truong Phan
(74) *Attorney, Agent, or Firm* — Greenblum & Bernstein, P.L.C.

(57) ABSTRACT

A hardness tester includes a CCD camera, a monitor, a clipper (a CPU and a clipping program), and a display controller (the CPU and a display control program). The CCD camera captures an image of an indentation formed on a surface of a specimen via field lenses. The monitor displays the image of the indentation captured by the CCD camera. The clipper clips a plurality of regions from the image of the indentation captured by the CCD camera, the plurality of regions each containing a respective vertex. The display controller simultaneously displays on the monitor images of the plurality of regions clipped by the clipper.

8 Claims, 10 Drawing Sheets

Partial display

HARDNESS TESTER FOR MAINTAINING IMAGE RESOLUTION BY USING IMAGE CLIPPING

CROSS-REFERENCE TO RELATED APPLICATIONS

The present application claims priority under 35 U.S.C. §119 of Japanese Application No. 2011-188460, filed on Aug. 31, 2011, the disclosure of which is expressly incorporated by reference herein in its entirety.

BACKGROUND OF THE INVENTION

1. Field of the Invention

The present invention relates to a hardness tester.

2. Description of Related Art

Conventionally, a hardness tester is known in which an indentation is formed by pressing an indenter into a surface of a specimen, and hardness of the specimen is measured based on dimensions of the indentation (see, for example, Related Art 1). For example, when a Vickers hardness tester is used to measure the hardness of the specimen, horizontal-direction alignment of the specimen is performed such that the formation position of the indentation in the surface of the specimen is directly below the indenter, and height-direction alignment (focusing) is performed on the formation position of the indentation. A turret is then rotated to position the indenter opposite the specimen, and a predetermined testing force is loaded on the surface of the specimen by the indenter to form the indentation. Thereafter, lengths of diagonal lines in the formed indentation are measured and the hardness is calculated based on the measured lengths of the diagonal lines in the indentation.

In such a hardness tester, an image of the surface of the specimen and of the indentation formed therein by the indenter is captured by a CCD camera and is displayed on a monitor. At this point, the image fed in from a megapixel camera (the CCD camera) has too many pixels and the full image cannot be displayed on the monitor of a size typically mounted in the hardness tester. Therefore, a method is used, for example, as shown in FIG. 9, in which pixels of a fed image G1 are dropped and an image in which the full image is scaled down (a reduced image) G2 is displayed on a monitor 81. However, in the method displaying the reduced image G2, resolution of the image suffers since pixels are dropped, and the capabilities of the CCD camera cannot be exploited. A method is known for a display method in which image resolution does not suffer, in which, for example, as shown in FIG. 10, a rectangular view B is set on top of the fed image G1 and only an image within the rectangular view B (partial image) G3 is displayed on a monitor 81. In this method, the partial image G3 displayed on the monitor 81 can be changed by displacing (scrolling) a position of the rectangular view B over the image G1.

SUMMARY OF THE INVENTION

However, in the method displaying only the partial image G3, only the area within the rectangular view B (one portion of the image) can be displayed, and so manual reading cannot be performed in which the length of the diagonal lines is measured by indicating a vertex (measurement point) of the indentation while a user views the image of the indentation.

The present invention provides a hardness tester capable of simultaneously displaying a plurality of measurement points within an image while preserving image resolution.

In order to address the above circumstance, one aspect of the present invention is a hardness tester measuring hardness of a specimen placed on a specimen stage by loading a predetermined testing force on a surface of the specimen with an indenter to form an indentation, then measuring dimensions of the indentation. The hardness tester includes an image capturer, a display, a clipper, and a display controller. The image capturer captures an image of the indentation formed in the surface of the specimen via field lenses. The display displays the image of the indentation captured by the image capturer. The clipper clips a plurality of regions from the image of the indentation captured by the image capturer, the regions containing measurement points. The display controller causes the display to simultaneously display images of the plurality of regions clipped by the clipper.

Another aspect of the present invention is the hardness tester in which the image of the indentation is a quadrilateral shape. The predetermined measurement points are vertices of the image of the indentation.

Another aspect of the present invention is the hardness tester in which the display controller is able to display both vertical guide lines extending in a vertical direction and horizontal guide lines extending in a horizontal direction overlaid on the image on the display.

Another aspect of the present invention is the hardness tester, further including an evaluator evaluating whether the predetermined measurement points are contained in each of the plurality of regions clipped by the clipper.

The present invention includes the clipper clipping the plurality of regions which contain the predetermined measurement points from the image of the indentation captured by the image capturer and the display controller causing the display to simultaneously display the plurality of regions clipped by the clipper. Therefore, the plurality of measurement points within the image can be simultaneously displayed by the display while preserving image resolution.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereafter, a hardness tester according to the present embodiment will be described in detail with reference to the drawings.

First, a configuration of a hardness tester 100 according to the present embodiment is described. Furthermore, in the following description, as shown in FIG. 1, left and right directions of the hardness tester 100 are an X direction, forward and backward directions are a Y direction, and a height direction is a Z direction.

Figure 1:
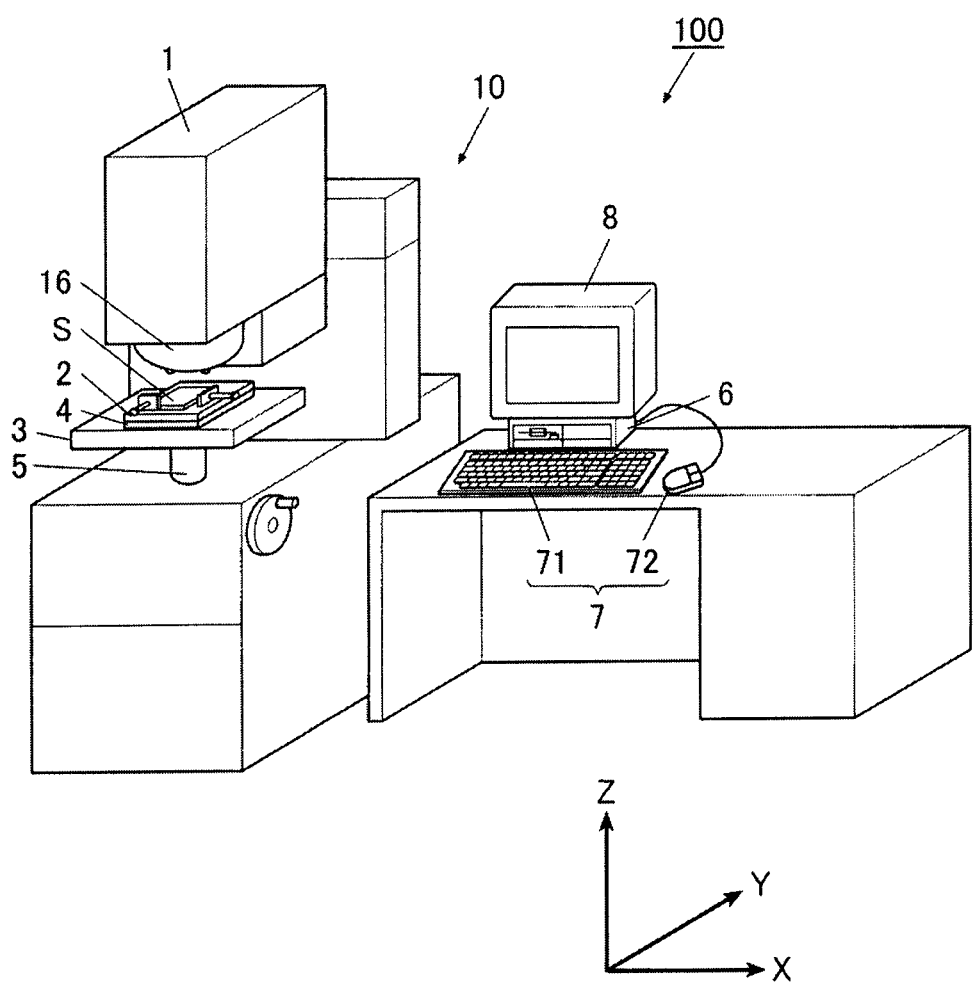
FIG. 1 is a schematic view showing an overall configuration of a hardness tester according to the present invention.

The hardness tester 100 is, for example, a Vickers hardness tester and, as shown in FIG. 1, includes a tester main body 10, a controller 6, an operator 7, a monitor 8, and the like.

Figure 2:
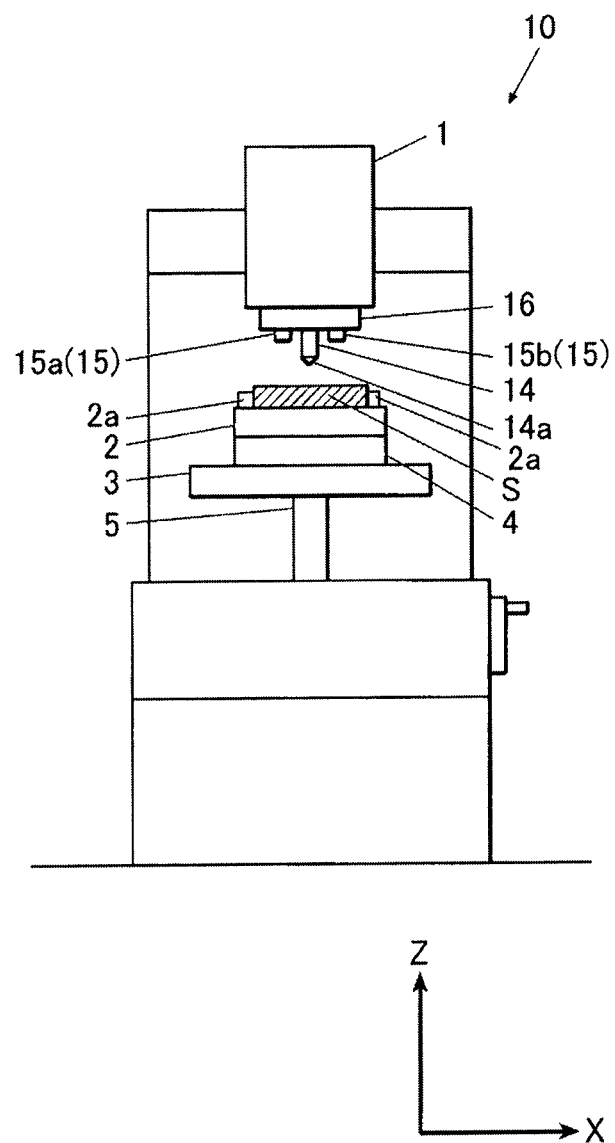
FIG. 2 is a schematic view showing a tester main body of the hardness tester in FIG. 1.

The tester main body 10 includes, for example and as shown in FIG. 2, a hardness measurer 1 performing a hardness measurement of a specimen S; a specimen stage 2 on which the specimen S is placed; an XY stage 3 displacing the specimen stage 2; an AF (Z) stage 4 for focusing on a surface of the specimen S; and a lift mechanism 5 lifting and lowering the specimen stage 2 (XY stage 3 and AF (Z) stage 4).

The hardness measurer 1, for example, includes an illumination device 11 illuminating the surface of the specimen S; a CCD (Charge Coupled Device) camera 12 capturing an image of the surface of the specimen S; an indenter shaft 14 which includes an indenter 14a; and field lenses 15. The hardness measurer 1 is further configured with a turret 16, which is able to switch between the indenter shaft 14 and the field lenses 15 by rotating.

The illumination device 11 illuminates the surface of the specimen S by irradiating light. The light irradiated from the illumination device 11 reaches the surface of the specimen S via a lens 1a, a half mirror 1d, a mirror 1e, and the field lenses 15.

Figure 3:
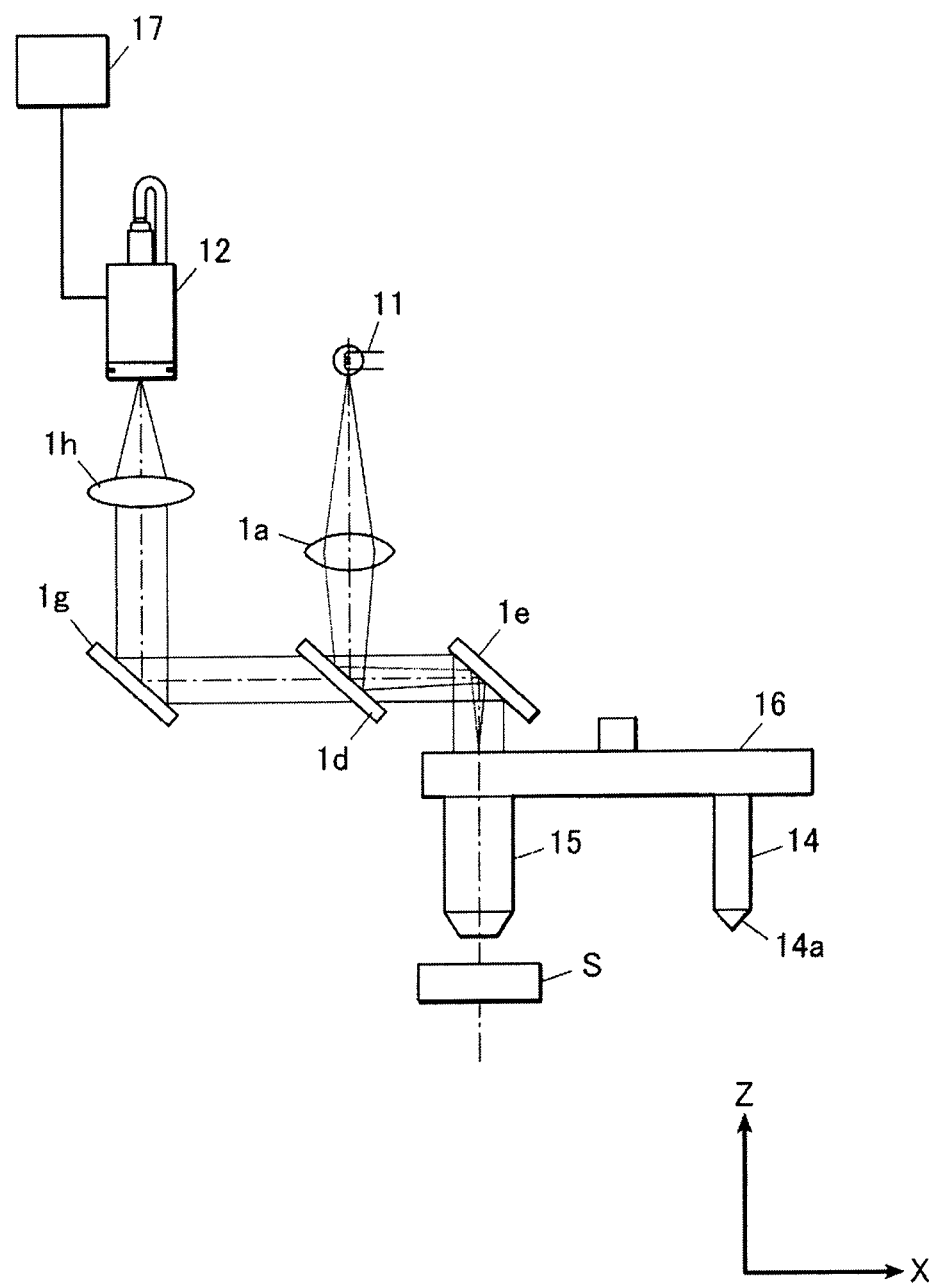
FIG. 3 is a schematic view showing a hardness measurer of the hardness tester in FIG. 1.

The CCD camera 12 is an image capturer. As shown in FIG. 3, for example, the CCD camera 12 captures an image of the surface of the specimen S and of an indentation formed thereon by the indenter 14a based on reflected light input from the surface of the specimen S via the field lenses 15, the mirror 1e, the half mirror 1d, a mirror 1g, and a lens 1h. The CCD camera 12 then acquires image data and outputs the image data to the controller 6 via a frame grabber 17, which is capable of simultaneously accumulating and storing image data for a plurality of frames.

The specimen S is placed on the specimen stage 2 and the indenter shaft 14 is displaced toward the specimen S by a loading mechanism (not shown in the drawings), which is driven in response to a control signal output by the controller 6. The indenter shaft 14 then presses the indenter 14a, which includes a tip portion, onto the surface of the specimen S with a predetermined testing force. The indenter 14a of the present embodiment has a tip having a quadrilateral spindle shape. Thus, in a plan view, a quadrilateral indentation is formed in the surface of the specimen S.

The field lenses 15 are collective lenses configured with differing powers of magnification. A plurality of field lenses 15 are supported on a lower surface of the turret 16 and, by being disposed above the specimen S through rotation of the turret 16, light irradiated from the illumination device 11 is uniformly irradiated on the surface of the specimen S. Specifically, the field lenses 15 are configured to include a high power field lens 15a and a low power field lens 15b having a magnification lower than the high power field lens 15a.

The turret 16 includes on the lower surface thereof the indenter shaft 14 and the plurality of field lenses 15 (the high power field lens 15a and the low power field lens 15b). By rotating around an axis in the Z-axis direction, the turret 16 is configured to be capable of switching to one of the indenter shaft 14 and the plurality of field lenses 15 in order to position the same above the specimen S. That is, the turret 16 is capable of forming the indentation in the surface of the specimen S by lowering the indenter shaft 14 in a state where the indenter shaft 14 is positioned above the specimen S, and is further capable of observing the formed indentation by positioning the field lenses 15 above the specimen S.

The specimen stage 2 includes a specimen holder 2a holding the specimen S which is placed on the top surface of the specimen stage 2. The XY stage 3 is driven by a driving mechanism (not shown in the drawings) driving the XY stage 3 in response to a control signal output by the controller 6. The specimen stage 2 is thus displaced in a direction (X direction or Y direction) perpendicular to a displacement direction (Z direction) of the indenter 14a. The AF stage 4 is driven in response to a control signal output by the controller 6 and, based on the image data captured by the CCD camera 12, minutely lifts and lowers the specimen stage 2 to focus on the surface of the specimen S. The lift mechanism 5 is driven in response to a control signal output by the controller 6 and changes the relative distance between the specimen stage 2 and the field lenses 15 by displacing the specimen stage 2 (the XY stage 3 and AF stage 4) in a vertical direction.

The operator 7 is configured to include a keyboard 71, a mouse 72, and the like, and is employed, for example, when a user defines various conditions for execution of a hardness test with the hardness tester 100. Defining various conditions means, for example, setting test conditions (values such as material of the specimen S, a testing force (N) to be loaded on the specimen S by the indenter 14a, and magnification powers of the field lenses 15), a test start point, a number of rows/columns, pitch, and the like. When a predetermined operation is carried out on the operator 7 by the user, a predetermined operation signal corresponding to the operation is output to the controller 6.

The monitor 8 is a display and may be configured with a display device such as an LCD (Liquid Crystal Display). The monitor 8 displays an image captured by the CCD camera 12 of the surface of the specimen S and an image of the indentation formed thereon. The monitor 8 also displays defined conditions for the hardness test input with the operator 7, results of the hardness test, and the like.

Figure 4:
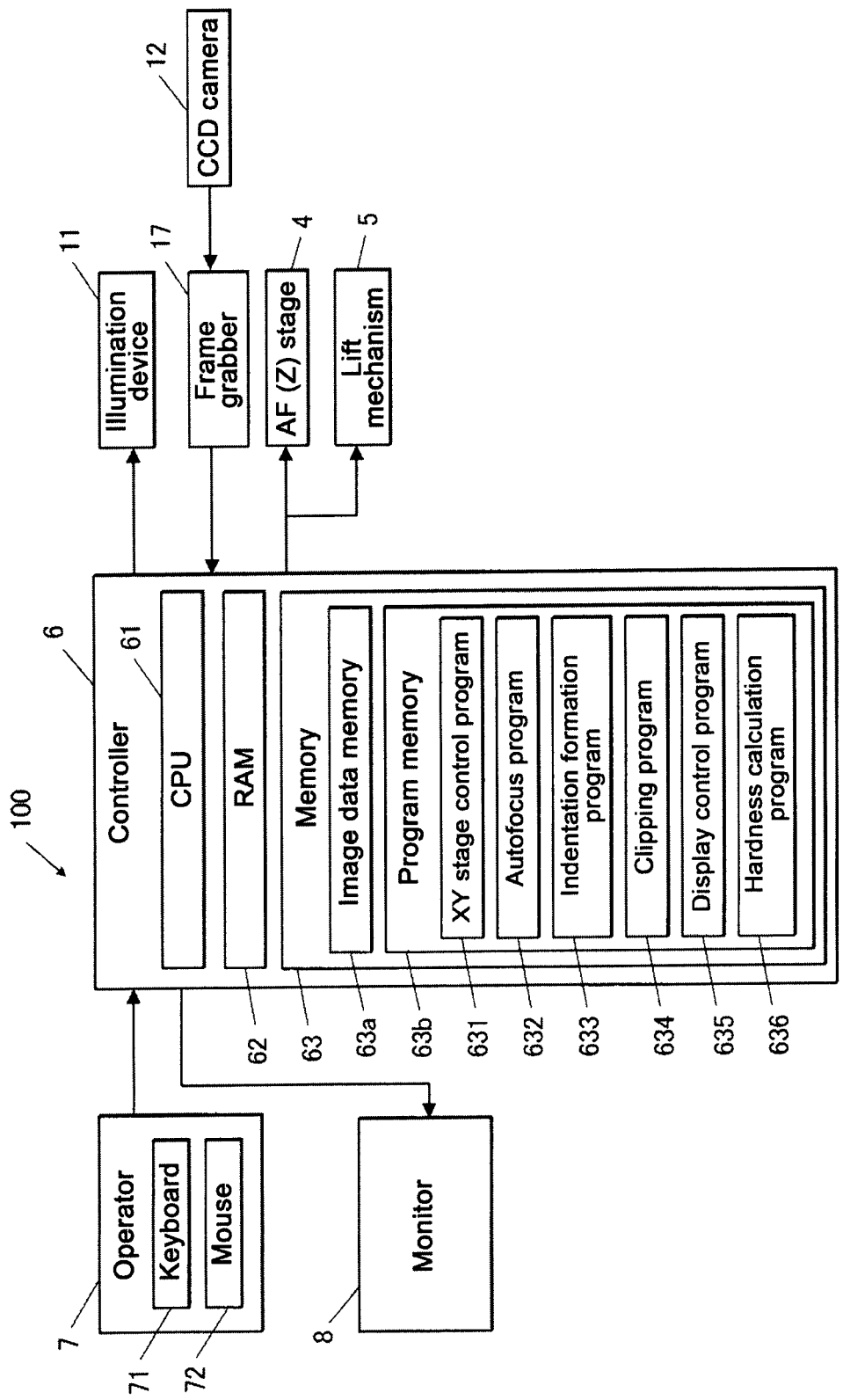
FIG. 4 is a block diagram showing a control structure of the hardness tester in FIG. 1.

As shown in FIG. 4, the controller 6 is configured to include a CPU (Central Processing Unit) 61, a RAM (Random Access Memory) 62, a memory 63, and the like. By executing a predetermined program stored in the memory 63, the controller 6 can perform operation control for the performance of a predetermined hardness test, and the like.

The CPU 61 reads a processing program, for example, stored in the memory 63, then performs overall control of the hardness tester 100 by loading and executing the processing program in the RAM 62.

The RAM 62 loads the processing program executed by the CPU 61 in a program storage region within the RAM 62. The RAM 62 also stores in a data storage region input data and processing results generated when the processing program is executed.

The memory 63 includes, for example, a storage medium (not shown in the drawings) configured with a semiconductor memory and the like for storing a program, data, and the like. The memory 63 stores various data, various processing programs, data processed by execution of the programs, and the like to enable the CPU 61 to perform overall control of the hardness tester 100.

Specifically, the memory 63 includes an image data memory 63a storing image data captured by the CCD camera 12 and a program memory 63b storing programs.

Image data for the image of the indentation formed on the surface of the specimen S, for example, is stored in the image data memory 63a.

An XY stage control program 631, an autofocus program 632, an indentation formation program 633, a clipping program 634, a display control program 635, and a hardness calculation program 636, for example, are stored in the program memory 63b.

The XY stage control program 631 is a program that, for example, allows the CPU 61 to control a position of the XY stage 3 such that, after the specimen S is placed on the specimen stage 2, the specimen S and the CCD camera 12 are opposite each other. Specifically, by executing the XY stage control program 631, the CPU 61 displaces the XY stage 3 such that a predetermined region on the surface of the specimen S is directly below the CCD camera 12.

The autofocus program 632 is a program that, for example, allows the CPU 61 to perform autofocusing with respect to the surface of the specimen S. Specifically, by executing the autofocus program 632, the CPU 61 lifts and lowers the AF stage 4 to perform autofocusing with respect to the surface of the specimen S based on image information obtained by the CCD camera 12 of the hardness measurer 1.

The indentation formation program 633 is a program that, for example, allows the CPU 61 to form the indentation in the surface of the specimen S. Specifically, by executing the indentation formation program 633, the CPU 61 presses the indenter 14a onto the surface of the specimen S with the predetermined testing force to form the indentation. Furthermore, in the present embodiment, because the indentation is formed having a quadrilateral shape in a plan view, an image of the quadrilateral indentation is captured. The image of the formed indentation is captured by the CCD camera 12 and the image data for the captured image of the indentation is stored in the image data memory 63a.

Figure 5:
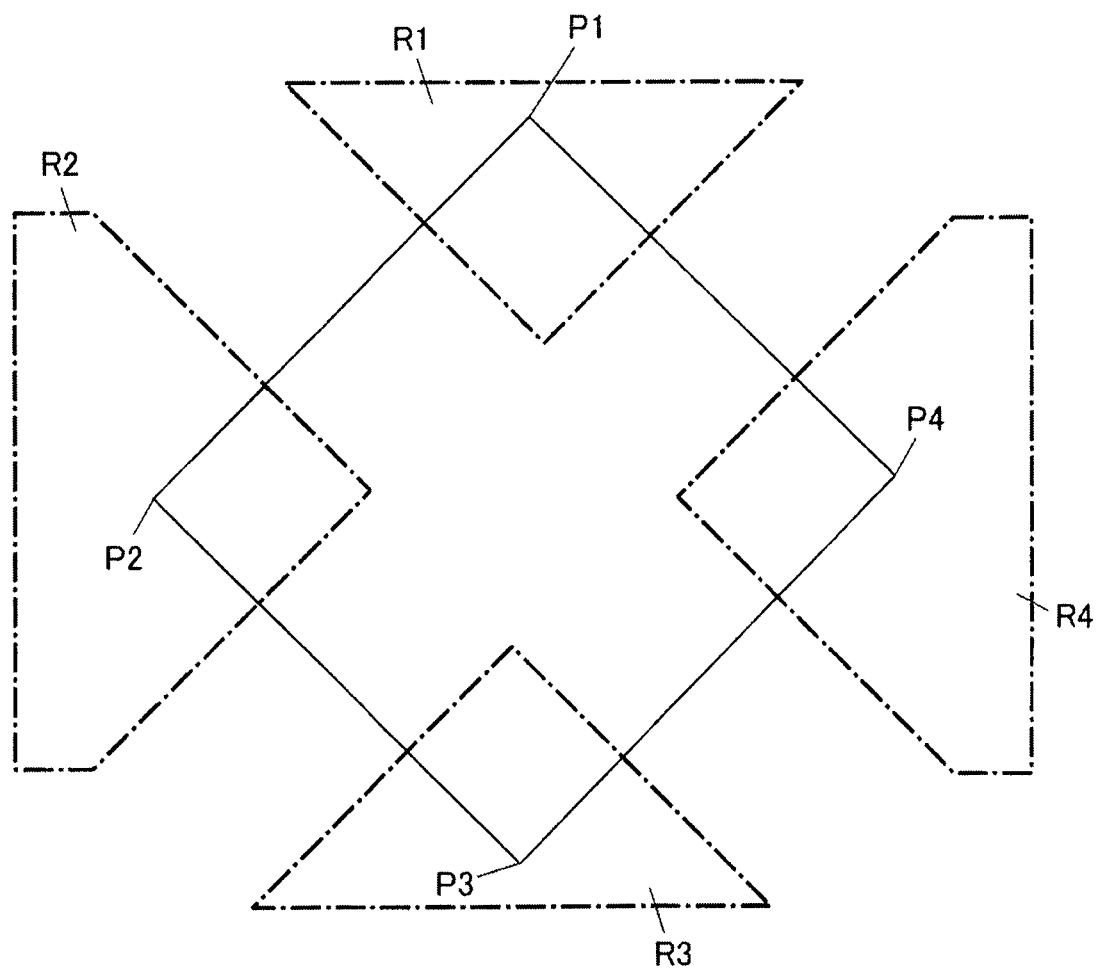
FIG. 5 is a conceptual diagram showing clipped regions of a captured image of an indentation.

The clipping program 634 is a program that, for example, allows the CPU 61 to clip a plurality of regions that contain predetermined measurement points from the image of the indentation captured by the CCD camera 12. FIG. 5 illustrates a conceptual diagram showing clipping regions of the captured image of the indentation. As shown in FIG. 5, by executing the clipping program 634, the CPU 61 clips four regions (clipping regions) R1-R4 which contain vertices P1-P4 of the image of the indentation as the predetermined measurement points. At this point, the position and shape of the clipping regions R1-R4 are predefined according to the shape of the indenter used in the hardness tester. For example, the present embodiment is a hardness tester in which an image of a quadrilateral indentation is captured. Therefore, four vertices of the indentation may be assumed to be positioned at central portions at each of a top and bottom portion of the captured image and at central portions at each of a left and right portion of the image. Three-sided clipping regions R1 and R3 are defined at the central portions at the top and bottom of the image, respectively, and five-sided clipping regions R2 and R4 are defined at the central portions at the left and right of the image, respectively. The CPU 61 acts as a clipper by executing this clipping program 634.

Figure 6:
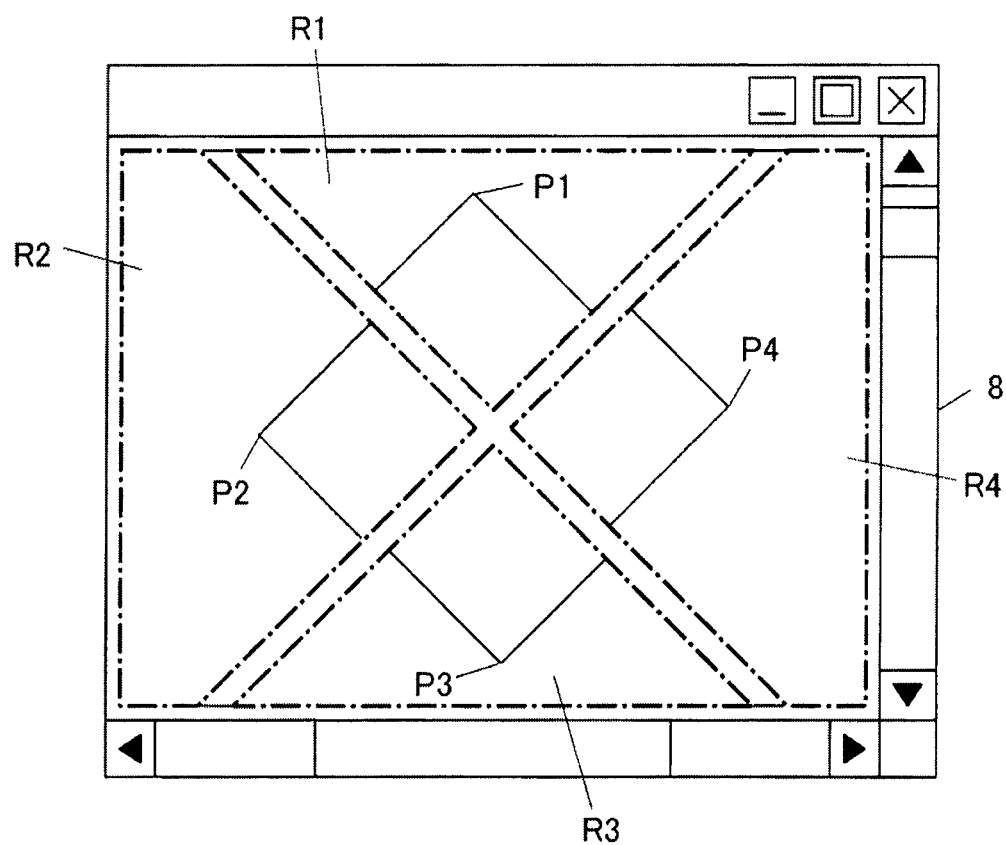
FIG. 6 is an example showing a state in which the clipped regions are displayed on a display.

The display control program 635 is a program that, for example, allows the CPU 61 to simultaneously display on the monitor 8 images of the plurality of regions (clipping regions R1-R4) clipped by the execution of the clipping program 634. Specifically, as shown in FIG. 6, by executing the display control program 635, the CPU 61 displays on the monitor images in which only the clipping regions R1-R4 have been extracted from the image of the indentation.

Figure 7:
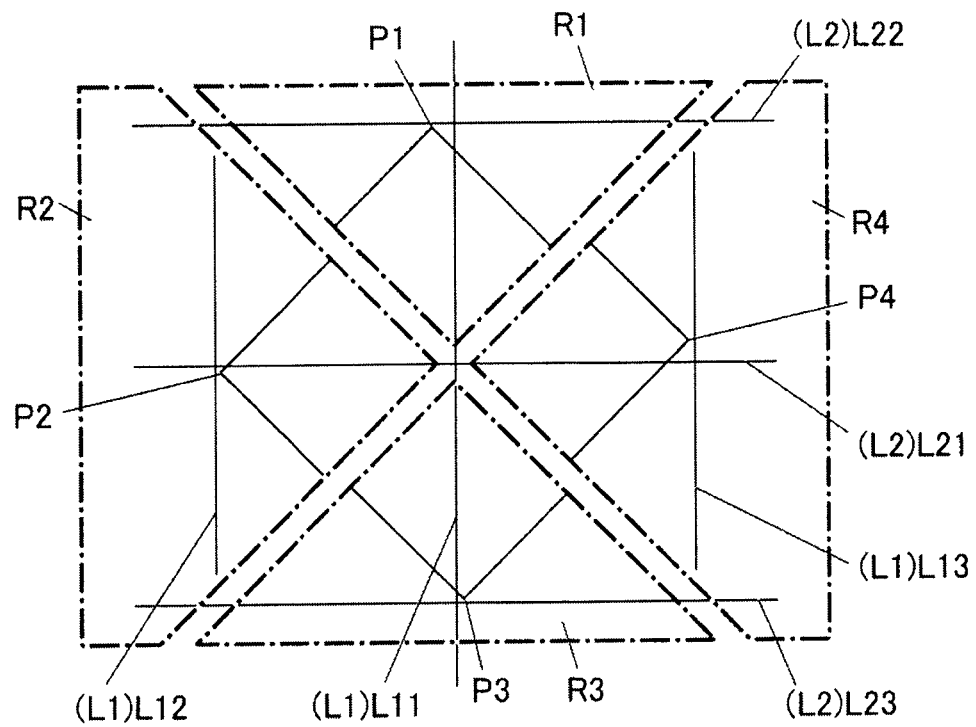
FIG. 7 is an example showing a state in which vertical guide lines and horizontal guide lines are displayed overlaid on the image displaying the clipped regions in FIG. 6.

As shown in FIG. 7, by executing the display control program 635, the CPU 61 is also able to display vertical guide lines L1 extending in the vertical direction and horizontal guide lines L2 extending in the horizontal direction overlaid on the images of the clipping regions R1-R4 displayed on the monitor 8. The vertical guide lines L1 include a central vertical guide line L11 defined so as to travel through the center in a width direction of the monitor 8; a left vertical guide line L12 parallel to the central vertical guide line L11 and defined so as to be positioned near the vertex P2; and a right vertical guide line L13 parallel to the central vertical guide line L11 and defined so as to be positioned near the vertex P4. The horizontal guide lines L2 include a central horizontal guide line L21 defined so as to travel through the center in a height direction of the monitor 8; a top horizontal guide line L22 parallel to the central horizontal guide line L21 and defined so as to be positioned near the vertex P1; and a bottom horizontal guide line L23 parallel to the central horizontal guide line L21 and defined so as to be positioned near the vertex P3. In response to an instruction operation from the user, the CPU 61 displays the guide lines L1 and L2. The user is able to align the positions of the vertices P1 and P3 and the positions of the vertices P2 and P4 using the guide lines L1 and L2.

The CPU 61 acts as a display controller by executing this display control program 635.

The hardness calculation program 636 is a program that, for example, allows the CPU 61 to measure the length of diagonal lines of the indentation from the image of the indentation and, based on the measured length of the diagonal lines of the indentation, to calculate hardness of the specimen S. Specifically, when the vertices P1-P4 of the indentation are indicated as measurement points by the user, for example, the CPU 61 executes the hardness calculation program 636 and measures the length of the diagonal lines of the indentation. Of course, the CPU 61 includes the pixel count for portions of the image not displayed on the monitor 8 in the calculations, as well. At this point, since the four vertices P1-P4 of the indentation are displayed on the monitor 8 simultaneously, the user is able to perform measurements of width and height while verifying the positions of the four vertices P1-P4.

Next, an effect of the hardness tester 100 of the present embodiment is described. In the hardness tester 100 having the above-described configuration, when the image of the indentation captured by the CCD camera 12 is displayed on the monitor 8, the plurality of clipping regions R1-R4 which contain the predetermined measurement points (the vertices P1-P4 of the image of the indentation) are clipped (see FIG. 5). Only the images of the clipping regions R1-R4 are then displayed on the monitor 8 (see FIG. 6). Therefore, there is no need to display the entire image captured by the CCD camera 12 and regions other than the clipping regions R1-R4 are not displayed. Thus, there is no need to drop pixels from the images for the clipping regions R1-R4 displayed on the monitor 8, and image resolution does not suffer. The images of the clipping regions R1-R4 displayed on the monitor 8 are images in which portions containing effective measurement points (vertices P1-P4) have been clipped from the image of the indentation. Vertices P1-P4 of the image of the indentation can all be verified simultaneously on the monitor 8.

In addition, when the images of the clipping regions R1-R4 are displayed on the monitor 8, the vertical guide lines L1 and the horizontal guide lines L2 can be displayed overlaid on the images. Therefore, the user can align the positions of opposing vertices (P1 with P3 and P2 with P4) and can perform measurements of the width and the height of the indentation while viewing the positions of the vertices P1-P4.

As described above, the hardness tester 100 of the present embodiment includes the CCD camera 12, the monitor 8, the clipper (the CPU 61 and the clipping program 634), and the display controller (the CPU 61 and the display control program 635). The CCD camera 12 captures an image of the indentation formed on the surface of the specimen S via the field lenses 15. The monitor 8 displays the image of the quadrilateral indentation captured by the CCD camera 12. The clipper (the CPU 61 and the clipping program 634) clips the plurality of regions R1-R4 from the image of the indentation captured by the CCD camera 12, the regions R1-R4 containing the vertices P1-P4 of the image of the indentation as the predetermined measurement points. The display controller (the CPU 61 and the display control program 635) simultaneously displays on the monitor 8 the plurality of regions R1-R4 clipped by the clipper. Therefore, the plurality of measurement points in the image (the vertices P1-P4 of the image of the indentation) can be simultaneously displayed on the monitor 8 while preserving image resolution. Accordingly, a manual read process in which the measurement points are manually selected can be executed accurately.

In addition, according to the hardness tester 100 of the present embodiment, the display controller is able to display the vertical guide lines L1 extending in the vertical direction and the horizontal guide lines L2 extending in the horizontal direction by overlaying the guide lines L1 and L2 on the image on the monitor 8. Therefore, the positions of opposing vertices (P1 with P3 and P2 with P4) can be aligned and measurement of the width and height can be performed while viewing the positions of the four vertices P1-P4 on the image.

Figure 8:
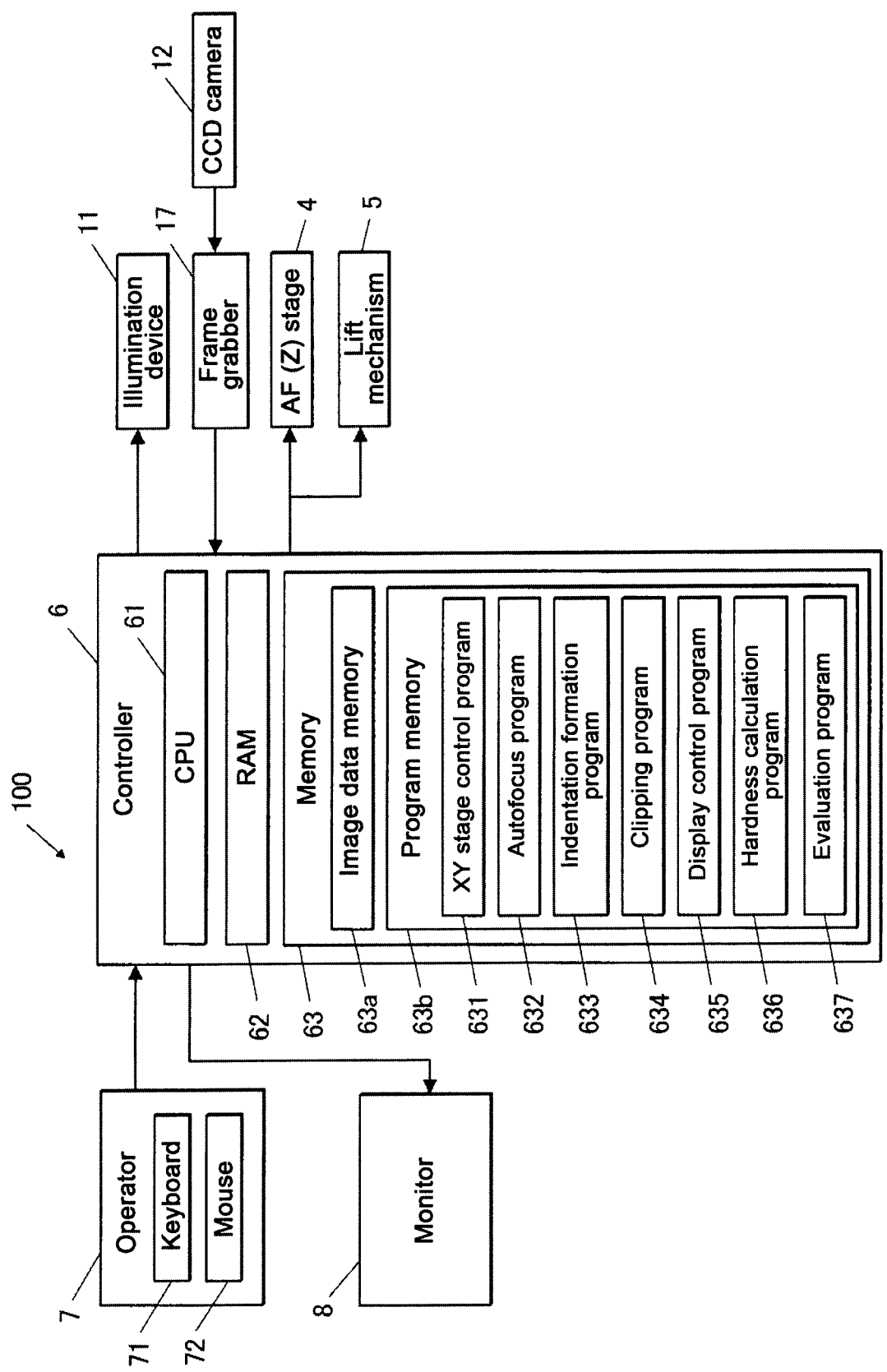
FIG. 8 is a block diagram showing a control structure of a hardness tester according to a modified example.
Figure 9:
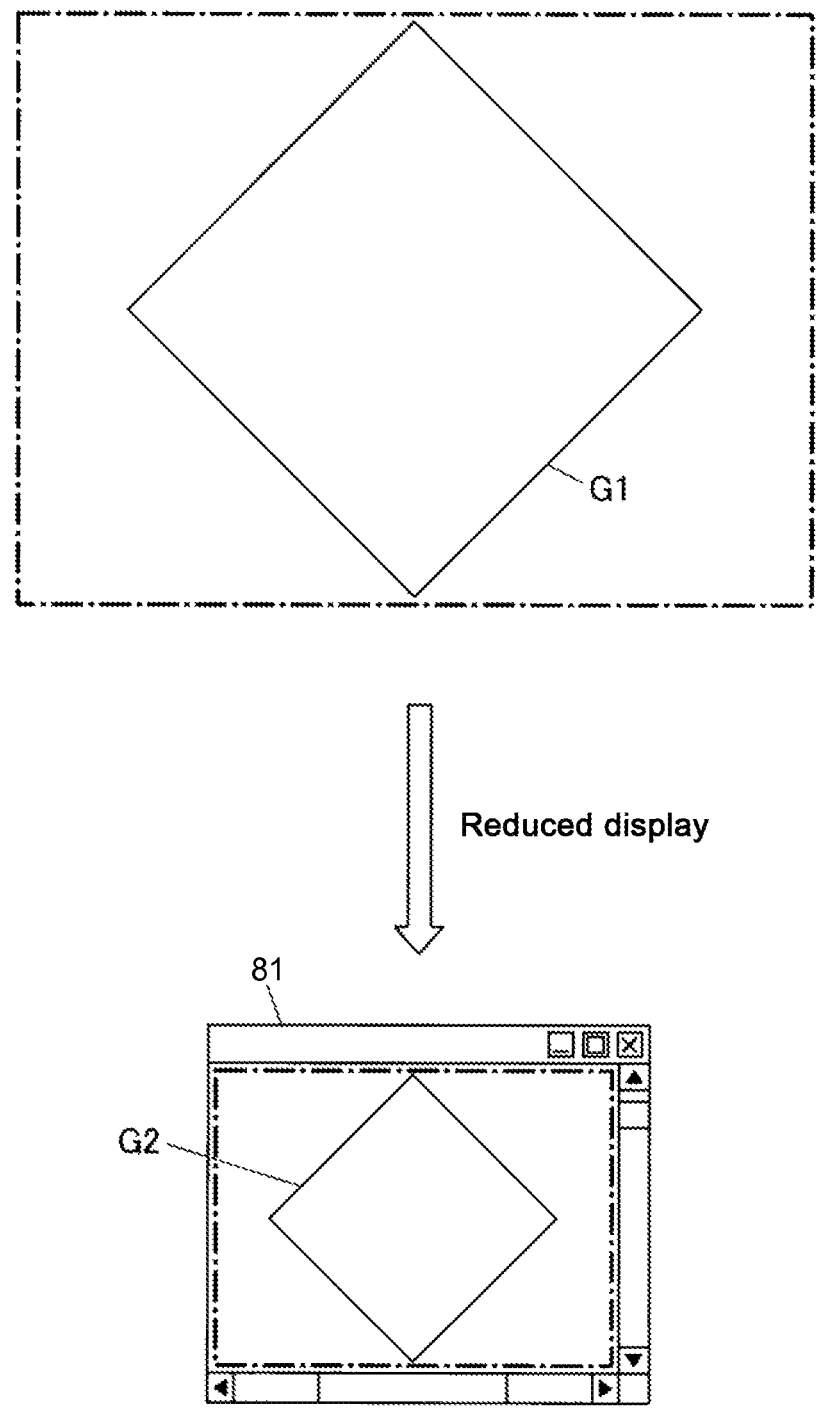
FIG. 9 is an explanatory diagram of a conventional image display method in a hardness tester.
Figure 10:
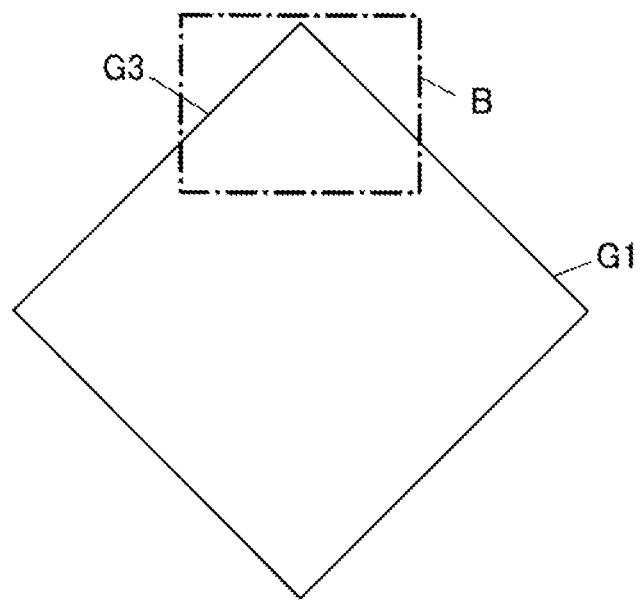
FIG. 10 is an explanatory diagram of a conventional image display method in a hardness tester.
Figure 10:
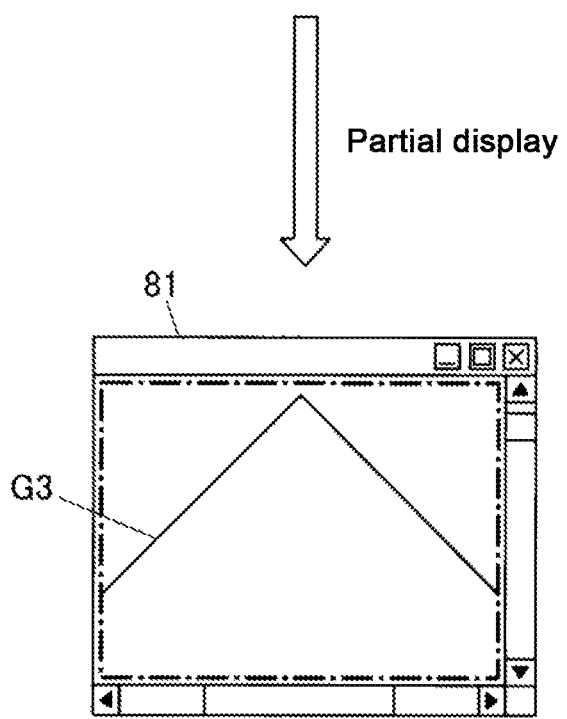

Moreover, as shown in FIG. 8, after the plurality of regions R1-R4 have been clipped by the clipper, before being displayed on the monitor 8, an evaluator (the CPU 61 and an evaluation program 637) may be further included, evaluating whether the predetermined measurement points (the vertices P1-P4 of the image of the indentation) are contained in each of the plurality of clipped regions R1-R4. Specifically, by executing the evaluation program 637, after the clipping regions R1-R4 are clipped, the CPU 61 determines whether the vertices P1-P4 of the image are contained by performing edge detection for each of the clipping regions R1-R4. In this way, even in a case where the capture positions are misaligned, processing can be performed to quickly recapture the image and the like.

In the embodiment described above, a case where the image of the indentation has a quadrilateral shape was described as an example. However, the shape of the image of the indentation is not limited to this. Specifically, the indenter is not limited to a quadrilateral spindle shape. In addition, the clipping regions may be defined according to a shape of an image of an indentation derived from the shape of an indenter. Further, in the above-described embodiment, a case where the clipping regions are defined with a three-sided shape and a five-sided shape was described as an example. However, the shape of the clipping regions is not limited to these.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester measuring hardness of a specimen placed on a specimen stage by loading a predetermined testing force on a surface of the specimen with an indenter to form an indentation, then measuring dimensions of the indentation, the hardness tester comprising:
   an image capturer configured to capture, via field lenses, an image of the indentation formed in the surface of the specimen;
   a display configured to display the image of the indentation captured by the image capturer;
   a clipper configured to clip a plurality of regions from the image of the indentation captured by the image capturer, each region of the plurality of regions containing a respective vertex, and the plurality of regions together comprises less than the image of the indentation; and
   a display controller configured to cause the display to simultaneously display images of the plurality of regions clipped by the clipper.

2. The hardness tester according to claim 1, wherein the image of the indentation is a quadrilateral shape.

3. The hardness tester according to claim 1, wherein the display controller is further configured to display both vertical guide lines extending in a vertical direction and horizontal guide lines extending in a horizontal direction overlaid on the image on the display.

4. The hardness tester according to claim 1, further comprising an evaluator configured to evaluate whether a said respective vertex is included in each of the plurality of regions clipped by the clipper.

5. The hardness tester according to claim 2, wherein the display controller is further configured to display both vertical guide lines extending in a vertical direction and horizontal guide lines extending in a horizontal direction overlaid on the image on the display.

6. The hardness tester according to claim 2, further comprising an evaluator configured to evaluate whether a said respective vertex is included in each of the plurality of regions clipped by the clipper.

7. The hardness tester according to claim 3, further comprising an evaluator configured to evaluate whether a said respective vertex is included in each of the plurality of regions clipped by the clipper.

8. The hardness tester according to claim 5, further comprising an evaluator configured to evaluate whether a said respective vertex is included in each of the plurality of regions clipped by the clipper.

\* \* \* \* \*